(12) United States Patent
Gilbertson

(10) Patent No.: US 6,795,171 B1
(45) Date of Patent: Sep. 21, 2004

(54) DEVICE FOR JUDGING SYMMETRY, BRIGHTNESS, AND EFFICIENCY OF LIGHT RETURN IN PRECIOUS STONES

(75) Inventor: Al Gilbertson, Carlsbad, CA (US)

(73) Assignee: EightStar Diamond Company, Inc., Cotati, CA (US)

( * ) Notice: Subject to any disclaimer, the term of this patent is extended or adjusted under 35 U.S.C. 154(b) by 371 days.

(21) Appl. No.: 09/653,130

(22) Filed: Aug. 31, 2000

Related U.S. Application Data

(63) Continuation-in-part of application No. 09/578,058, filed on May 24, 2000.

(51) Int. Cl.$^7$ .............................................. G01N 21/00
(52) U.S. Cl. ...................................................... 356/30
(58) Field of Search ........................... 356/30, 31, 416, 356/419

(56) References Cited

U.S. PATENT DOCUMENTS

| | | | | |
|---|---|---|---|---|
| 4,647,194 A | * | 3/1987 | Shigetomi et al. | 356/30 |
| 5,196,966 A | * | 3/1993 | Yamashita | 359/896 |
| 5,260,763 A | * | 11/1993 | Yamashita | 356/30 |
| 5,430,538 A | * | 7/1995 | Kobayashi | 356/30 |
| 6,348,964 B1 | * | 2/2002 | Wagner et al. | 356/30 |
| 6,665,058 B1 | * | 12/2003 | Gilbertson | 356/30 |

* cited by examiner

*Primary Examiner*—Frank G. Font
*Assistant Examiner*—Layla Lauchman
(74) *Attorney, Agent, or Firm*—Miller Nash LLP

(57) ABSTRACT

The invention is a multicolored reflecting surface that can be mounted beneath a lens for facilitating the grading of a gemstone's brightness and symmetry. The multicolored reflective surface may be a disc that has an opening or aperture surrounded by multicolored concentric rings through which the gemstone is viewed on the object side of the lens. Alternatively, the multicolored reflective surface may be a cylinder formed of multicolored bands through which the gemstone is viewed. Light reflecting from the multicolored rings or bands creates specific colors on the gemstone that allow symmetry and brightness of the stone to be evaluated.

5 Claims, 9 Drawing Sheets

DARK BLUE

DEVICE FOR JUDGING SYMMETRY, BRIGHTNESS, AND EFFICIENCY OF LIGHT RETURN IN PRECIOUS STONES

CROSS-REFERENCE TO RELATED APPLICATION

This application is a continuation-in-part of application Ser. No. 09/578,058, filed May 24, 2000. The benefit of the filing date of that application is hereby claimed.

TECHNICAL FIELD OF THE INVENTION

The present invention relates to a device for observing and analyzing the quality of precious stones, especially diamonds, and in particular to a device which provides relevant information regarding a stone's symmetry, brightness, and efficiency of light return.

BACKGROUND OF THE INVENTION

While a significant part of a diamond's value is determined by its weight or carat, the popularity of diamonds as gem stones is due in large part to their inestimable brilliance. The degree of a diamond's brilliance is influenced significantly by its cut, transparency, clarity, and color.

When diamonds are cut to traditional "ideal" cut angles and the facets are carefully aligned to facilitate "mirroring," light leakage can be minimized and a greater percentage of light will be returned to the viewer, thereby giving the diamond a brighter appearance. "Mirroring" refers to the reflection of light to form symmetrical geometric patterns, wherein the facets work together to collect light and return the maximum amount of light to the viewer.

Brightness, however, is a function of several attributes of cutting. Even though light may not be "leaking" or passing through the rear side ("pavilion") of the diamond, there is no guarantee that large amounts of light are being returned to the viewer. In order to evaluate the efficiency of light return, light must be gathered from around the viewer, and its reflective pattern analyzed.

A variety of devices have been invented for judging the brilliancy of diamonds. One such device, described in U.S. Pat. No. 4,647,194, relates to the judging of brilliancy in diamonds by viewing a stone through a magnifying lens wherein the object side of the lens is fitted with a solid red colored disc having a centrally-located hole. Viewing the diamond through the lens assembly provides the viewer with an image of the diamond in which those areas which are reflecting light to the viewer appear as red, whereas those areas of the diamond not reflecting light, but leaking light through the pavilion, appear colorless. This observation allows the viewer to form a general conclusion about the light reflective properties or brilliancy of the particular stone.

An additional device, described in U.S. Pat. No. 5,260,763, permits a user to observe a diamond through a magnifying lens positioned over or near the end of a tubular device with the diamond or other gemstone located at the opposite end. Light reflecting from the cylindrical interior of the tube creates a pattern on the surface of the gemstone that is ultimately reflected to the overhead viewer. This instrument employs a solid-colored surface such as red or silver to form reflective patterns on the gemstone so that an observer may form a general conclusion regarding the light reflective properties or brilliancy of the particular stone being observed.

The prior art devices are limited in their ability to produce an image which permits the angles of reflective light to be analyzed. Consequently, no information is available regarding the stone's symmetry or the efficiency of light return based on the cut of the diamond, or other gemstone. Without such information, faults in a gemstone's cut may not be apparent, particularly to an inexperienced purchaser. Such faults may significantly impact the appearance of the gem stone and detract from its total value.

SUMMARY OF THE INVENTION

It is an object of the present invention to address the aforementioned problem and provide a device with which a viewer may judge a stone's brightness and symmetry via the observed efficiency of light return from various angles of incidence upon a diamond or other gemstone. The device embodied by the present invention is an improvement over prior art devices in that the reflective surface incorporates two or more distinctive colors arranged in a pattern which, when reflected from the surface of a gemstone to an overhead viewer, produces an image of a color pattern on the gemstone representative of the gemstone's symmetry.

An embodiment of the present invention comprises a simple body wherein a precious stone such as a diamond is placed between a light source and a magnifying lens. The lens is equipped, on the object side, with a multicolored disc wherein each color represents a ring around a portion of the disc, and wherein the stone is viewed through a centrally-located hole in said disc. The multicolored disc may also incorporate color patterns other than rings which provide information about the symmetry of a gemstone or parts thereof.

Light from a light source is reflected from each colored ring onto the diamnond's surface at an angle defined by the ring's position from the center of the disc through which the observer views the diamond. Because each angle or range of angles is represented by a specific color, light return efficiency can be analyzed and the symmetry and brightness of the stone evaluated.

In an alternate embodiment of the invention, the multicolored reflective surface takes the form of a cylinder through which a gemstone such as a diamond is viewed. Observation of a gemstone positioned at or near one end of the cylindrical multicolored surface is facilitated by a magnifying lens positioned at or near the opposite end of the cylindrical reflective surface.

An additional objective of the present invention is to provide a means of photographing gemstones and their reflective symmetry patterns by incorporating a camera in place of the magnifying lens described above in an embodiment made to facilitate such photography.

Other objects, advantages, and features of the present invention will be apparent to the reader from the foregoing and the appended claims, and as the ensuing detailed description and discussion of the invention proceeds in conjunction with the accompanying drawings.

BRIEF DESCRIPTION OF THE DRAWINGS

In the drawings, like reference numerals refer to like parts throughout the various views unless indicated otherwise, and wherein.

DETAILED DESCRIPTION OF THE INVENTION

Figure 1:
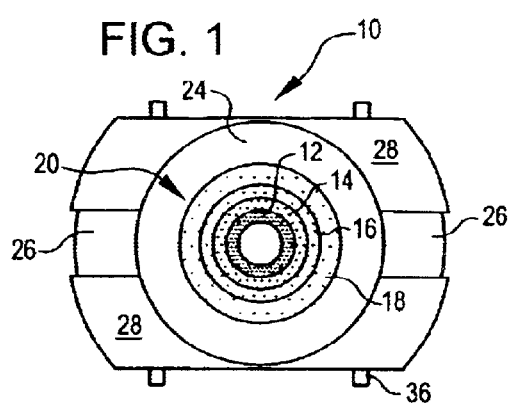
FIG. 1 is a bottom plan view of a lens bracket embodying the principles of the present invention.
Figure 1A:
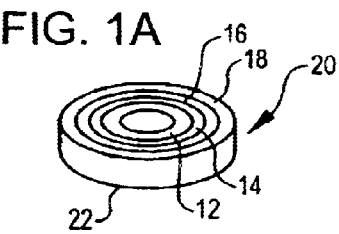
FIG. 1A is a perspective view of a multicolored reflecting disc.

Referring now to the drawings, FIG. 1 illustrates the underside of a lens bracket generally at 10. Colored rings 12, 14, 16, and 18 are fixedly secured to the surface of a disc 20 (see FIG. 1A) via an adhesive or other appropriate method. Disc 20 is a cylinder, open at one end 22, and capable of being fitted and frictionally secured to the object side of a magnifying lens 30 (see FIGS. 3, 4). In an alternative to securing the colored rings to the surface of disc 20, the disc itself may be constructed from a material having multicolored reflective areas in accordance with the principles of the present invention.

Figure 8:
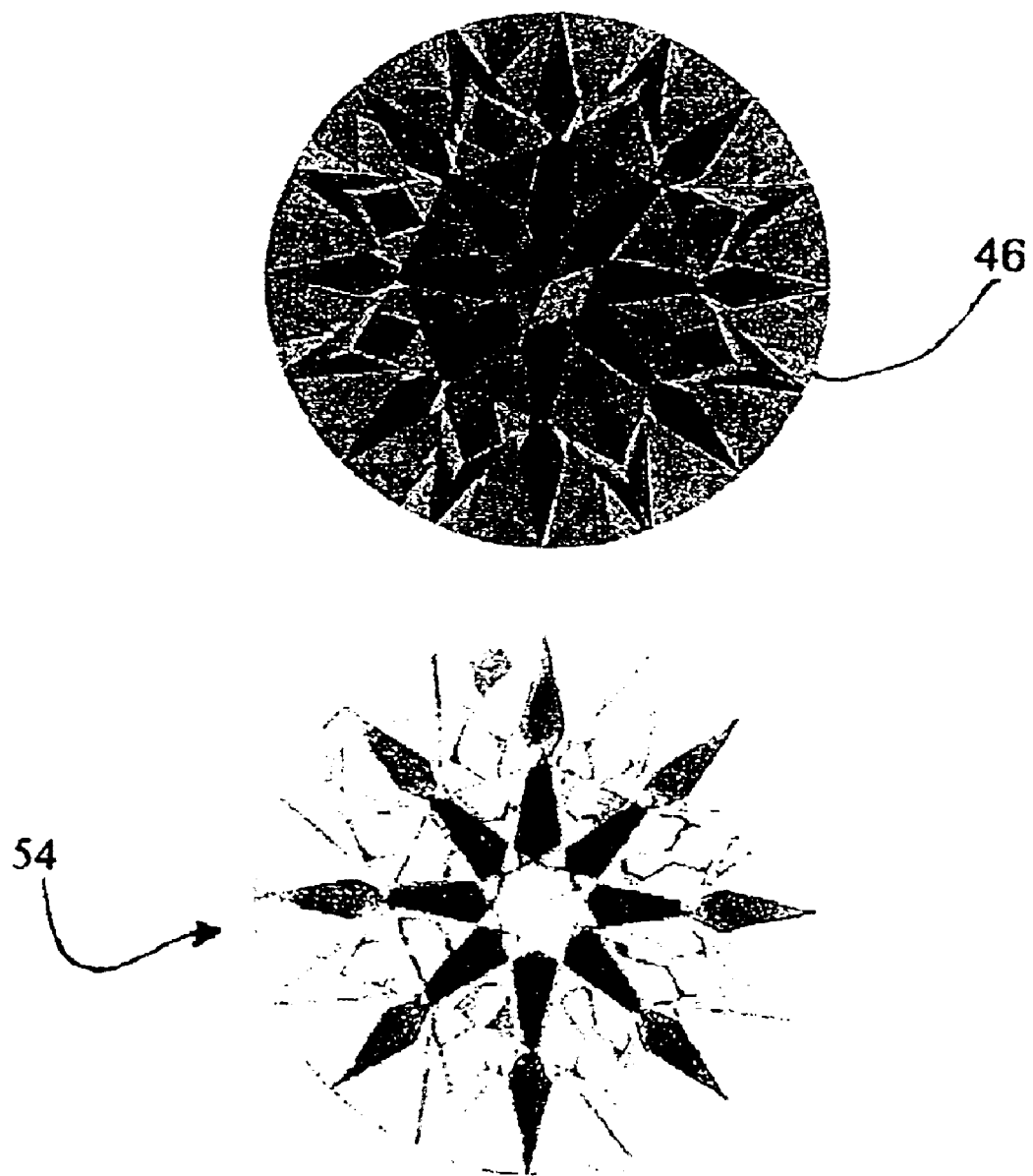
FIG. 8, like FIGS. 5–7, illustrates the image of an observed diamond with the black portion of the image shown separately.

The colors respectively associated with each ring of the disc 20 are irrelevant, but should be chosen to easily permit the observer to distinguish between the various colors since each color represents a distinct range of angles from which light is incident upon the top surface ("table") of the diamond. In the present embodiment used for illustrative purposes herein, each ring is associated with the following color: Ring 12 is red; ring 14 is green; ring 16 is dark blue; and ring 18 is light blue. The multicolored rings 12, 14, 16, and 18 define at least two differently colored areas on the disc surface 20 facing away from the lens 30 and toward the gemstone. Circular recess 24 and longitudinally extending slot 26 of lens bracket 10 are also colored similarly to the outermost ring 18, in this case light blue. The remaining portion 28 of the underside of lens bracket 10 is outside the critical angle and is not reflected to the overhead viewer by the diamond. This portion of the lens bracket is black in color. It should be noted that the overhead viewer may in fact observe a black reflection from the diamond as illustrated in FIG. 8. This black portion of the image is formed by reflected light that entered the diamond from 90 to 75 degrees to the table and generally represents the image of the overhead viewer as he or she observes the diamond through magnifying lens 30.

Figure 2:
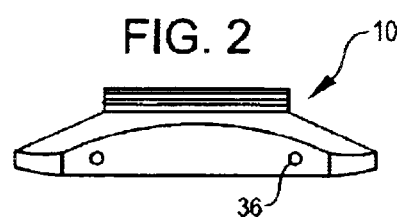
FIG. 2 is a side elevational view of the lens bracket illustrated in FIG. 1.
Figure 3:
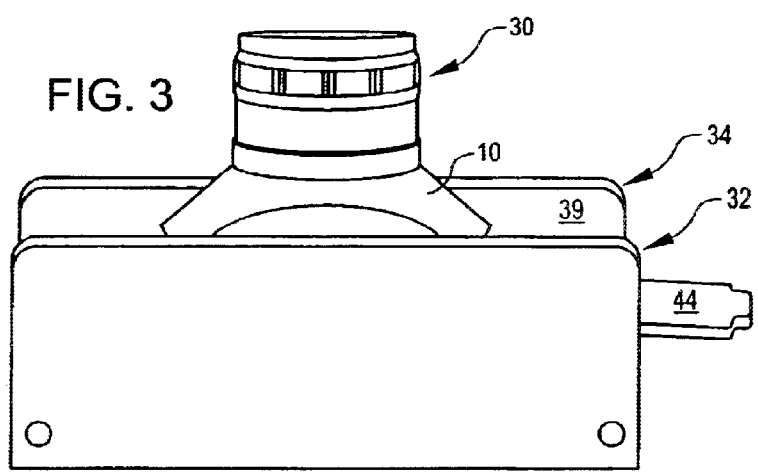
FIG. 3 is a front perspective view of a viewing device which may incorporate the principles of the present invention.
Figure 4:
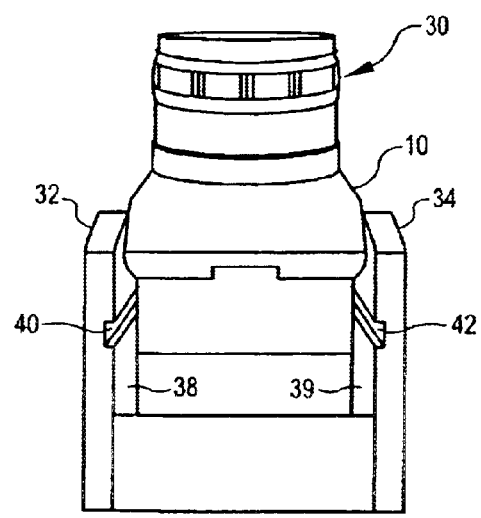
FIG. 4 is a side perspective view of the device illustrated in FIG. 3.

Referring now primarily to FIGS. 2–4, lens bracket 10 is mounted between a first grooved side wall 32 and a second grooved side wall 34. Lens bracket 10 is secured between first and second grooved side walls 32, 34 by extending pins 36 which are received in spaced openings (not shown) machined into the inner surfaces 38, 39 of grooved side walls 32, 34. Grooves 40, 42 extend longitudinally along the inner surfaces 38, 39 of grooved side walls 32, 34 to receive sliding plate 44.

A row of conical depressions (not shown) machined into the surface of sliding plate 44 support diamonds of various sizes and permit the user to position a particular stone directly below magnifying lens 30 for observation. After the selected diamond has been positioned below magnifying lens 30, the user activates a light source located below the diamond and sliding plate 44, and can then evaluate the symmetry, brightness, and sufficiency of light return for the particular stone.

Figure 5:
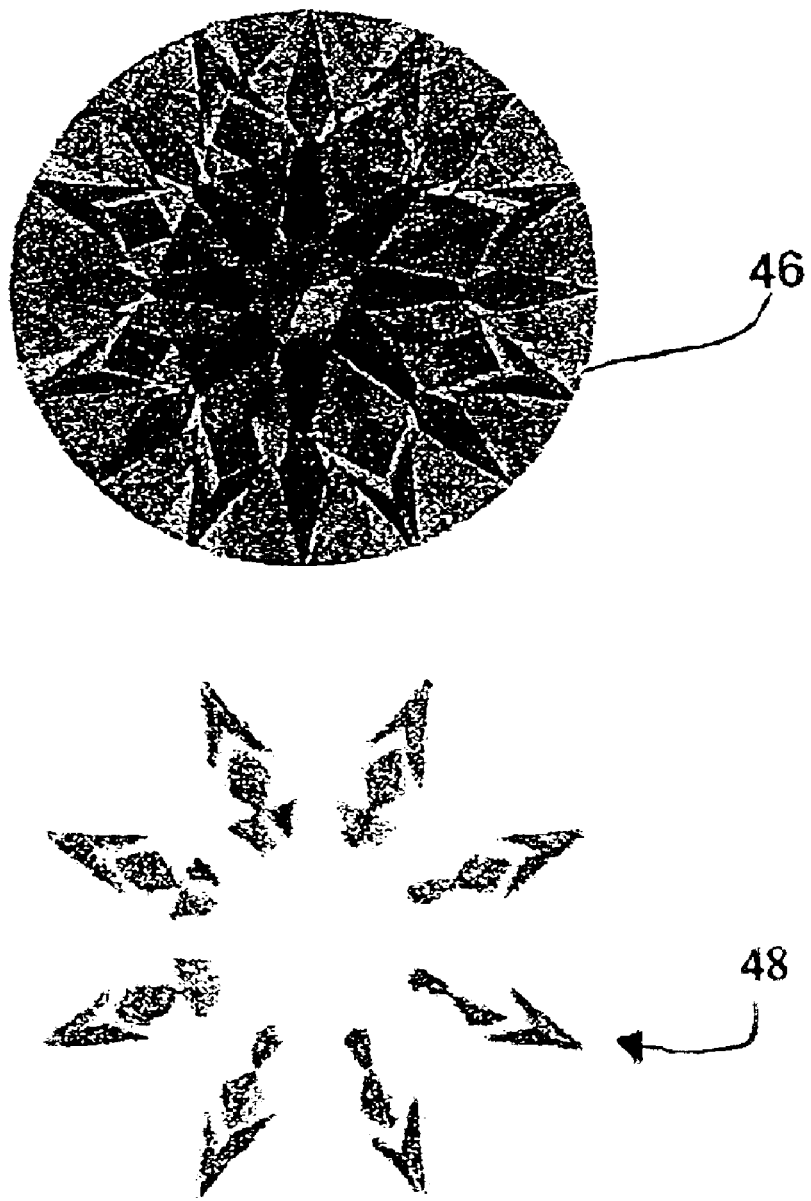
FIG. 5 illustrates the image of an observed diamond with the red portion of the image shown separately.
Figure 6:
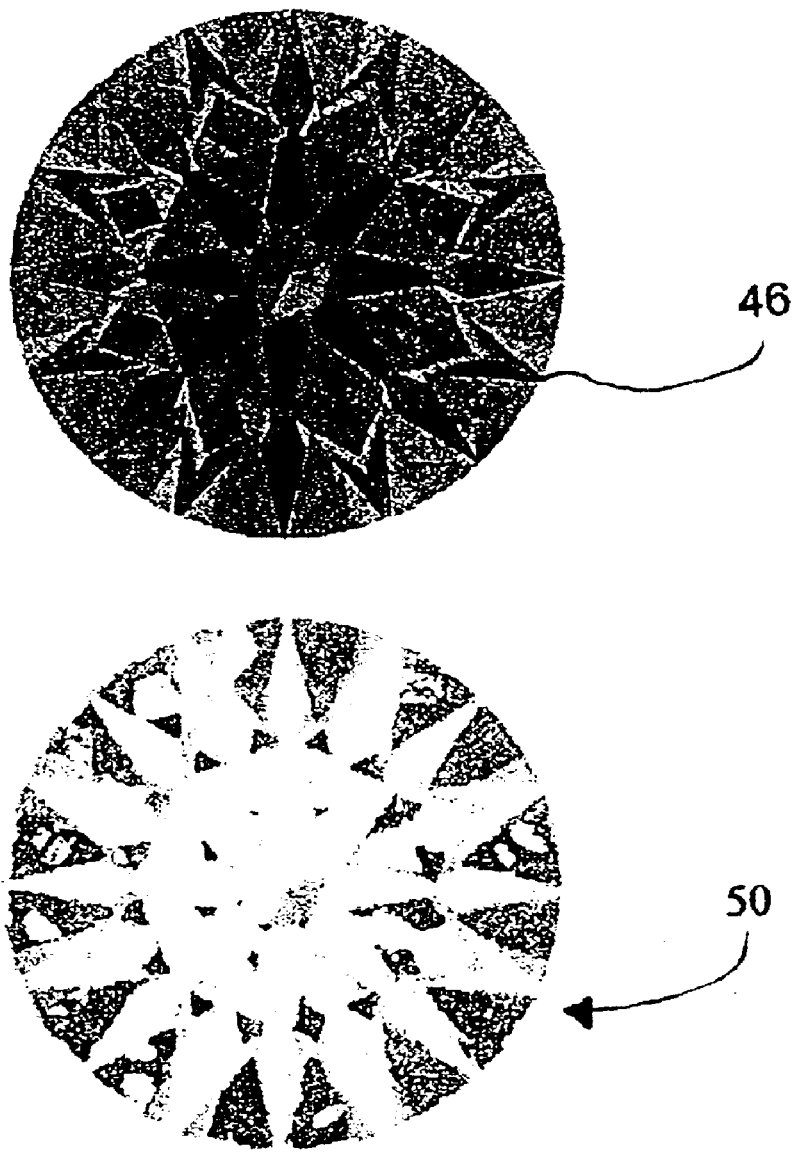
FIG. 6, like FIG. 5, illustrates the image of an observed diamond with the green portion of the image shown separately.
Figure 7:
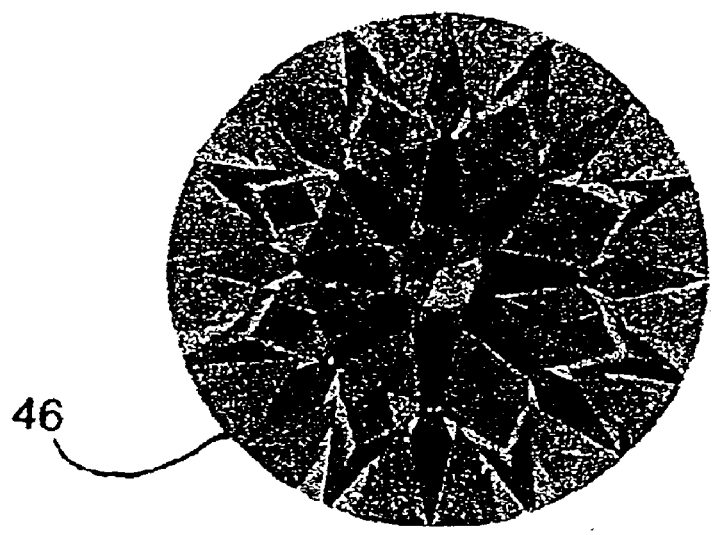
FIG. 7, like FIGS. 5 and 6, illustrates the image of an observed diamond with the dark blue portion of the image shown separately.
Figure 7:

Turning now to FIGS. 5–8, the image of a substantially symmetrical diamond 46 is illustrated in association with the separate image of a portion of the light reflected to the overhead viewer. The multicolored image of the substantially symmetrical diamond 46 is a composite of light incident upon the crown of the diamond from all angles greater than the critical angle. This image is that which is observed by the overhead viewer. In correspondence with the illustrative selected colors set forth above, FIG. 5 illustrates the red portion of the image 48 which is that light that is incident upon the crown of the diamond from 75 to 65 degrees and then reflected directly to the overhead viewer. FIG. 6 illustrates the green portion of the image 50 which is that light that is incident upon the crown of the diamond from 65 to 55 degrees and then reflected directly to the overhead viewer. FIG. 7 illustrates the dark blue portion of the image 52 which is that light that is incident upon the crown of the diamond from 55 to 45 degrees and then reflected directly to the overhead viewer. FIG. 8 illustrates the black portion of the image 54 which is that light that is incident upon the crown of the diamond from 90 to 75 degrees and then reflected directly to the overhead viewer. The remainder of the composite image 46 consists of light blue portions representing light incident upon the crown of the diamond at less than 45 degrees, but greater than the critical angle.

Figure 9:
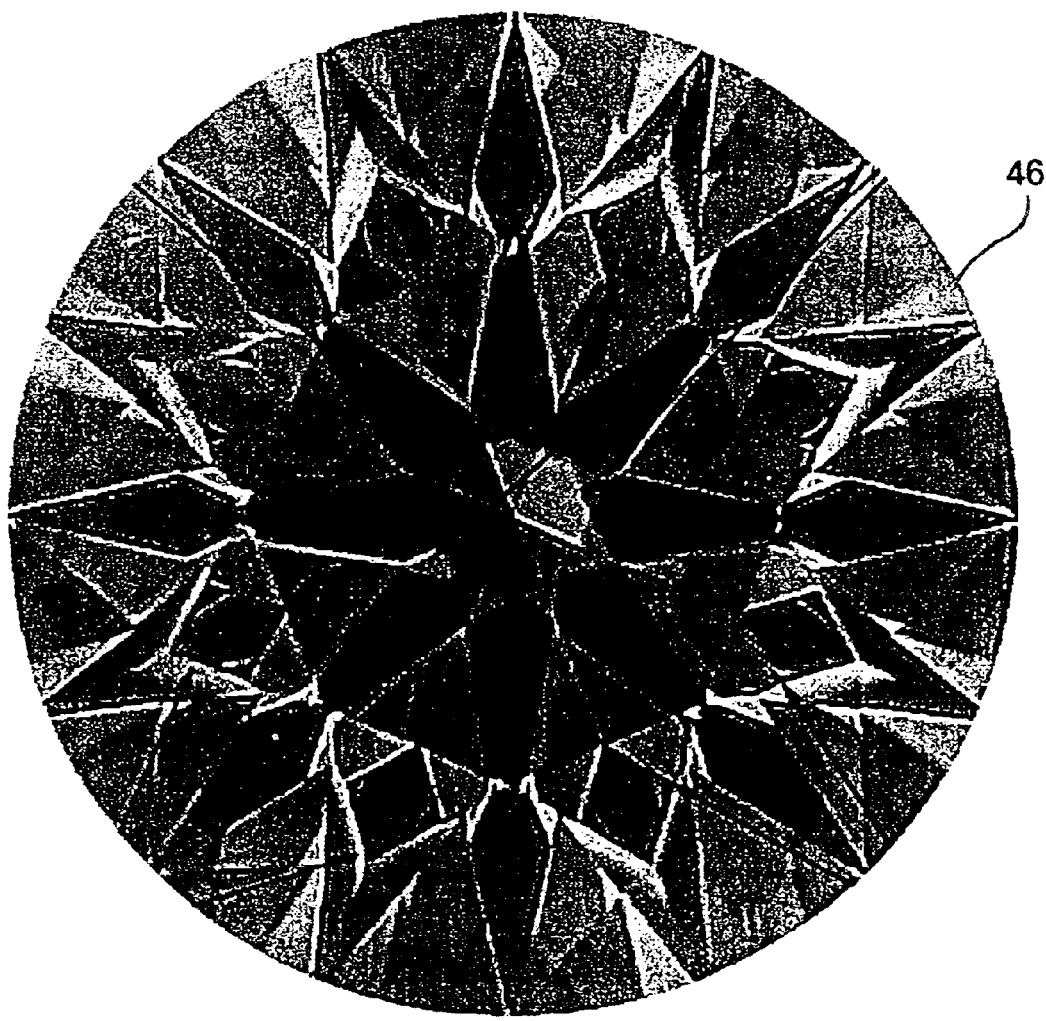
FIG. 9 illustrates the image of an observed diamond that is substantially symmetrical.
Figure 10:
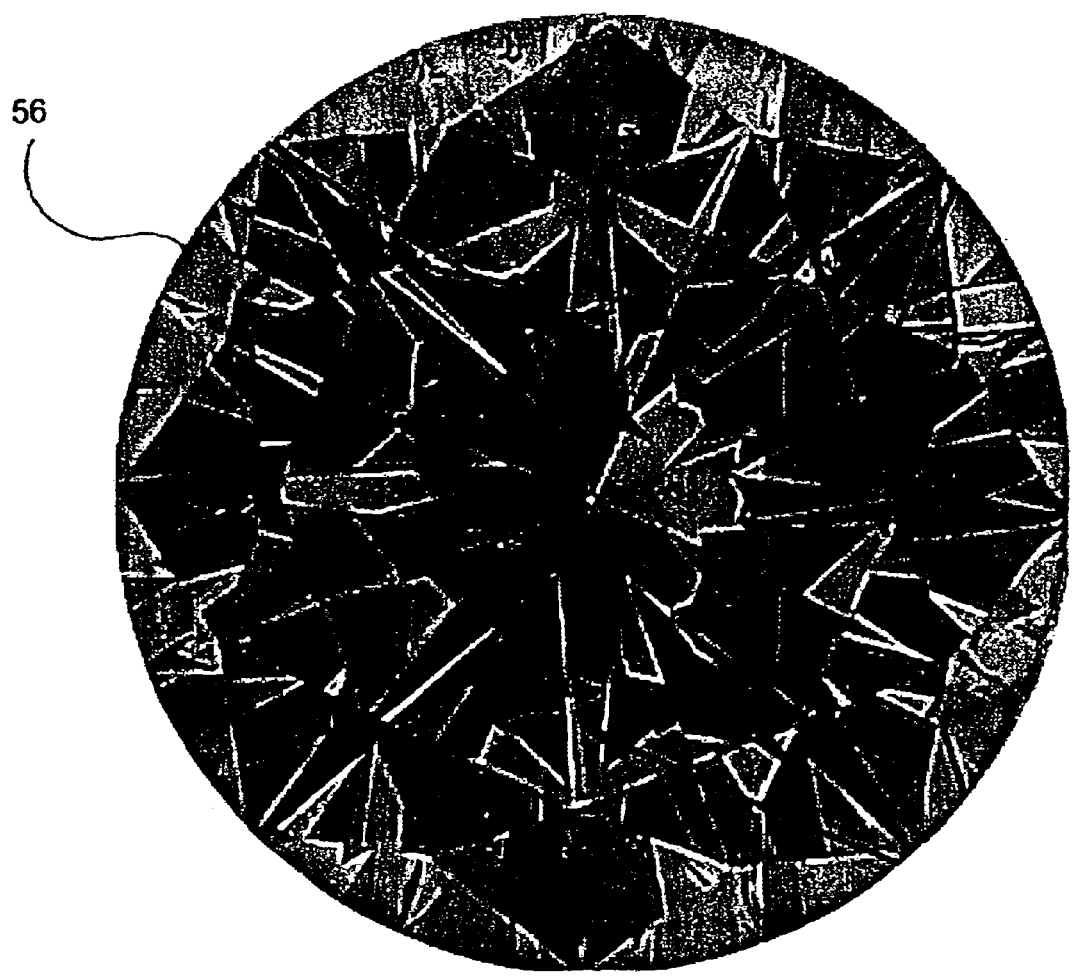
FIG. 10 illustrates the image of an observed diamond that is less symmetrical than the diamond illustrated in FIG. 9.

FIG. 9 is a larger image of the multicolored composite image illustrated at 46 in FIGS. 5–8 demonstrating the symmetrical nature of the particular gemstone viewed through magnifying lens 30. FIG. 10 illustrates the multicolored composite image 56 of a less symmetrical diamond as viewed under the same conditions through the magnifying lens. The erratic table reflections shown in this image illustrate the lack of symmetry in this particular gemstone. Such erratic reflections limit the brilliance of the stone and may detract from its overall value.

Figure 11:
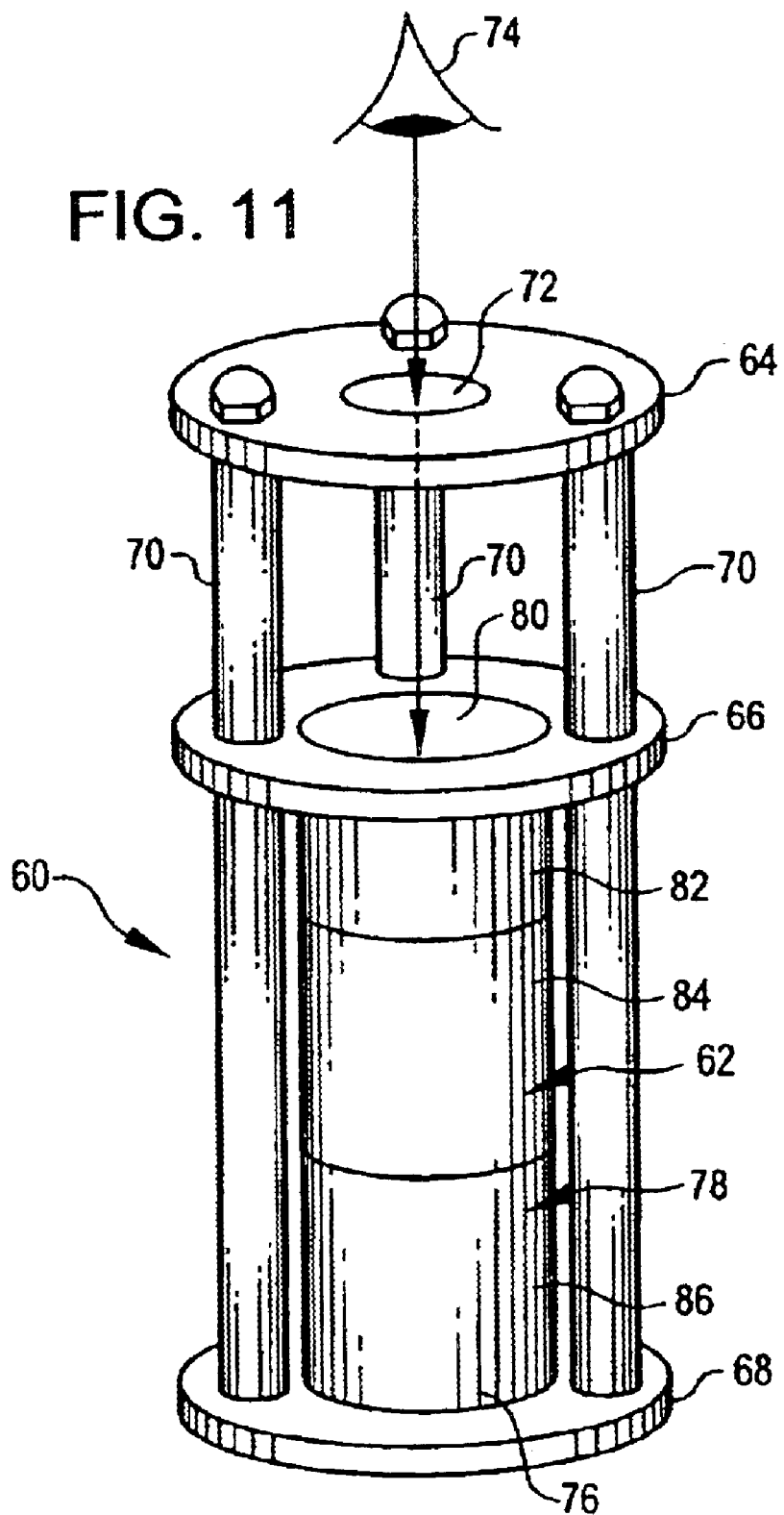
FIG. 11 is a perspective view of an alternate embodiment of the present invention wherein the multicolored reflective surface is a cylinder through which a gemstone is viewed.

In an alternative embodiment of the invention, illustrated generally at 60 in FIG. 11, the multicolored reflective surface 62 takes the form of a cylinder through which a gemstone such as a diamond may be viewed by an overhead observer.

A device embodying this alternative configuration may be constructed from a series of plates 64, 66, and 68, each of which contains a centrally located opening therein. The plates are spaced apart and secured together by a plurality of longitudinally extending bolts 70. The uppermost plate 64 contains an opening 72 through which an overhead viewer 74 may observe the reflected image of a gemstone such as a diamond located at the lower end 76 of cylinder 78.

The middle plate 66 also contains an opening into which is secured a lens 80 which magnifies the observed image of the gemstone to the overhead viewer 74. A pattern similar to that shown in FIG. 9 is produced by the multicolored reflective surface 62, and reflected to the overhead viewer through cylinder 78, lens 80, and opening 72.

Cylinder 78 may be constructed from a material to form the multicolored reflective surface 62, or preferably, from a material such as plastic wherein the cylindrically shaped multicolored reflective surface 62 can then be inserted into the cylinder 78 through an opening (not shown) in lower plate 68. This opening in lower plate 68 also provides a means for receiving a gemstone to be viewed into the cylinder. The device is simply placed over the gemstone to be viewed, which may be located on a plate having conical depressions for receiving gemstones as described above in association with the previous embodiment.

The spaced relationship of plates 64 and 66 provide an opening through which light is admitted to the cylinder 78 for reflection from surface 62 and the gemstone. This embodiment of the present invention is designed to facilitate the observation of gemstones without requiring an additional lightsource beneath the gemstone.

The multicolored reflective surface is preferable made up of a plurality of cylindrical bands of various colors. The respective colors are irrelevant, but should be chosen so, that each may be easily distinguished from another when observing the symmetrical pattern reflected from the surface of the gemstone being viewed. In a preferred embodiment, three cylindrical bands 82, 84, 86 form the reflective surface 62. For purposes of illustration only, the uppermost band 82 is red, the middle band 84 is green, and the lowermost band 86 is blue.

Figure 12:
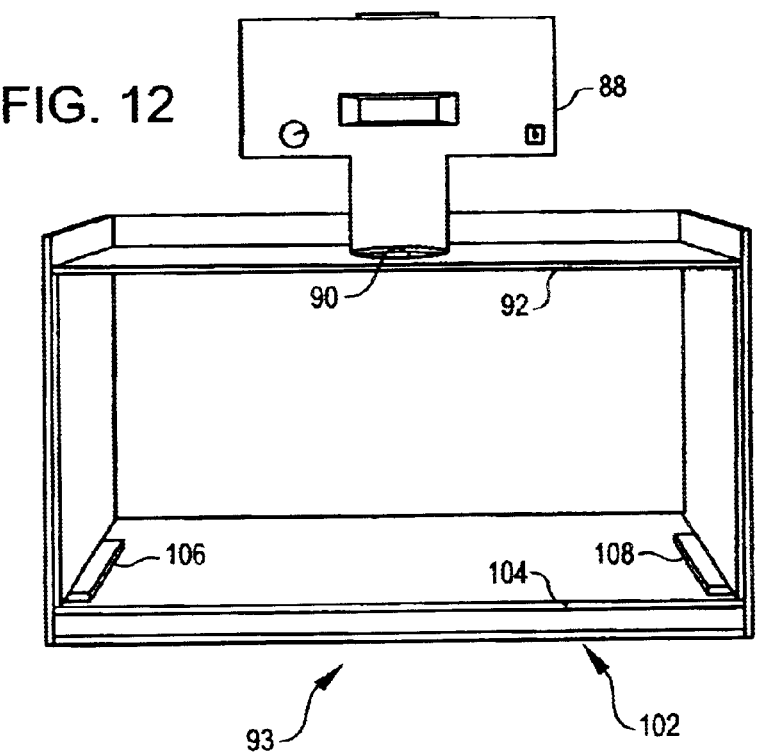
FIG. 12 is a top front perspective view of an embodiment of the present invention designed to facilitate the photographing of gemstones.
Figure 13:
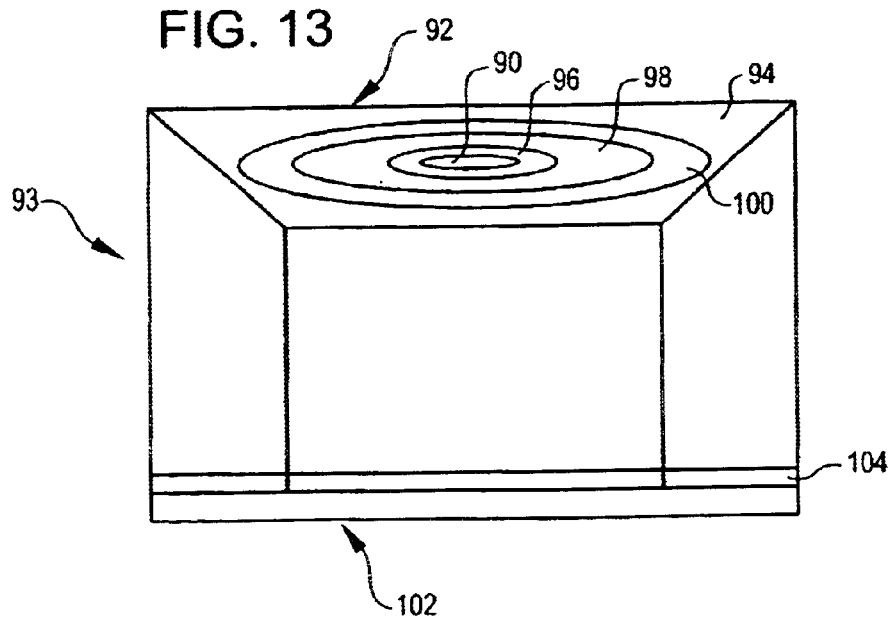
FIG. 13 is a bottom front perspective view of the device shown in FIG. 12 illustrating the multicolored reflective surface.

Referring now to FIGS. 12 and 13, the invention disclosed herein may also be employed to facilitate the photography of a gemstone's symmetry. Either embodiment described above could be incorporated into a device in which the respective magnifying lens is replaced with a camera's lens for photographing the reflected image of the gemstone. FIG. 12 illustrates such a configuration with a camera 88 positioned over an opening 90 in an upper plate 92 which displays a plurality of concentric rings of various colors on the underside 94 thereof (see FIG. 13). A front panel (not shown) has been removed from the box 93 illustrated generally in FIGS. 12 and 13 to show the interior thereof. In a preferred embodiment, the concentric rings 96, 98, 100 are colored red, green, and dark blue respectively, while the remainder of the interior of the box is light blue in color.

A light source is intended to be employed from the underside 102 of the box 93. This underside is constructed from a transparent material such as a plastic. A removable plate 104 facilitates the insertion and positioning of the gemstone beneath the camera for photographing each respective gemstone, and is supported on either side by parallel beams 106,108 which extend into the interior of box 93.

The multicolored rings or bands define at least two differently colored areas on the disc 20, or cylindrical surface 62. While it is believed that the concentric or cylindrical, multicolor ring arrangements described above are preferred for the respective embodiments, it may be possible to accomplish the same function by simply using different colored surface areas that have another geometric arrangement. Therefore, while the invention is described and illustrated here in the context of diamonds, and with particular color selections for the rings of the multicolored disc and the bands of the cylindrical reflective surface, the invention may be embodied in many forms without departing from the spirit or essential characteristics of the invention. The present embodiments are therefore to be considered in all respects as illustrative and not restrictive. The scope of the invention is indicated by the appended claims rather than by the foregoing description, and all changes which come within the meaning and range of equivalency of the claims are intended to be embraced therein.

What is claimed is:

1. An invention used in conjunction with a lens for judging a gemstone's brightness and symmetry, comprising:

a cylindrical surface directly attached to the object side of a lens forming an opening through which a gemstone is viewable on the object side of said lens, and wherein said surface is comprised of a plurality of bands, at least one of said bands having a different color from another.

2. An invention used in conjunction with a lens for judging a gemstone's brightness and symmetry, comprising:

a cylindrical surface directly attached to the object side of a lens forming an opening through which a gemstone is viewable on the object side of said lens, and wherein said surface is comprised of a plurality of colored areas, at least one of said areas having a different color from another.

3. An invention used in conjunction with a lens for judging a gemstone's brightness and symmetry, comprising:

a surface directly attached to the object side of the lens forming an opening through which a gemstone is viewable on the object side of said lens, and wherein said surface is comprised of a plurality of areas, at least one of said areas having a different color from another.

4. An apparatus comprising the combination of an invention for judging a gemstone's brightness and symmetry and a lens usable in conjunction with said invention, the invention being defined in claim 1, and the lens being a camera lens.

5. An apparatus comprising the combination of an invention for judging a gemstone's brightness and symmetry and a lens usable in conjunction with said invention, the invention being defined in claim 2, and the lens being a camera lens.

* * * * *